United States Patent [19]
Coleman

[11] Patent Number: 5,701,924
[45] Date of Patent: Dec. 30, 1997

[54] APPARATUS AND METHOD FOR DETECTING AND HANDLING LIQUID SEPARATION IN LIQUID EMULSIONS

[75] Inventor: Gerald N. Coleman, Peoria, Ill.

[73] Assignee: Caterpillar Inc., Peoria, Ill.

[21] Appl. No.: 739,846

[22] Filed: Oct. 30, 1996

[51] Int. Cl.⁶ ............................................. F17D 1/00
[52] U.S. Cl. .................. 137/3; 137/563; 137/101.25; 137/154; 366/137
[58] Field of Search .................... 137/3, 563, 98, 137/101.25, 154; 366/136, 137

[56] References Cited

U.S. PATENT DOCUMENTS

| | | |
|---|---|---|
| 593,333 | 11/1897 | Park. |
| 3,253,606 | 5/1966 | Kuntz ............................ 137/115 |
| 3,344,659 | 10/1967 | Chambers ......................... 73/61.1 |
| 3,721,121 | 3/1973 | Fierfort ............................ 73/155 |
| 3,826,133 | 7/1974 | Nicolas et al. .................... 73/152 |
| 3,911,256 | 10/1975 | Jones ............................ 235/151.3 |
| 3,942,374 | 3/1976 | Glenn, Jr. ........................ 73/155 |
| 4,953,975 | 9/1990 | Levine et al. ..................... 356/246 |
| 4,960,513 | 10/1990 | Young ............................. 210/104 |
| 4,982,755 | 1/1991 | Roberts et al. ................... 137/3 |
| 5,057,858 | 10/1991 | Woog ............................. 137/563 |
| 5,114,239 | 5/1992 | Allen ............................. 366/136 |
| 5,156,114 | 10/1992 | Gunnerman ....................... 123/1 |
| 5,251,488 | 10/1993 | Haberman et al. ............... 73/861.04 |
| 5,284,492 | 2/1994 | Dubin ............................. 44/301 |
| 5,564,462 | 10/1996 | Storch ............................ 137/563 |

FOREIGN PATENT DOCUMENTS 430301   5/1975   U.S.S.R. .

*Primary Examiner*—Denise L. Ferensic
*Assistant Examiner*—Ramyar M. Farid
*Attorney, Agent, or Firm*—Fred J. Baehr

[57] ABSTRACT

An apparatus and method for detecting and handling liquid separation in a liquid emulsion disposed in a tank 1 by preventing separated liquid from entering a withdrawal conduit 3 disposed in the lower portion of the tank 1 by a apparatus comprising a pump 9 driven by an electric motor 15 and taking its suction form the lower portion of the tank 1 and discharging adjacent the central portion of the tank 1, a float 5, which sinks in the emulsion and floats on the high density liquid is cooperatively associated with a relay 17 to start the pump motor 15 when accumulated high density liquid raises the float 5 a predetermined amount, a time delay 21 runs the pump 9 a predetermined length of time sufficient to reemulsify the accumulated high density and preventing it from entering the withdrawal conduit 3.

6 Claims, 1 Drawing Sheet

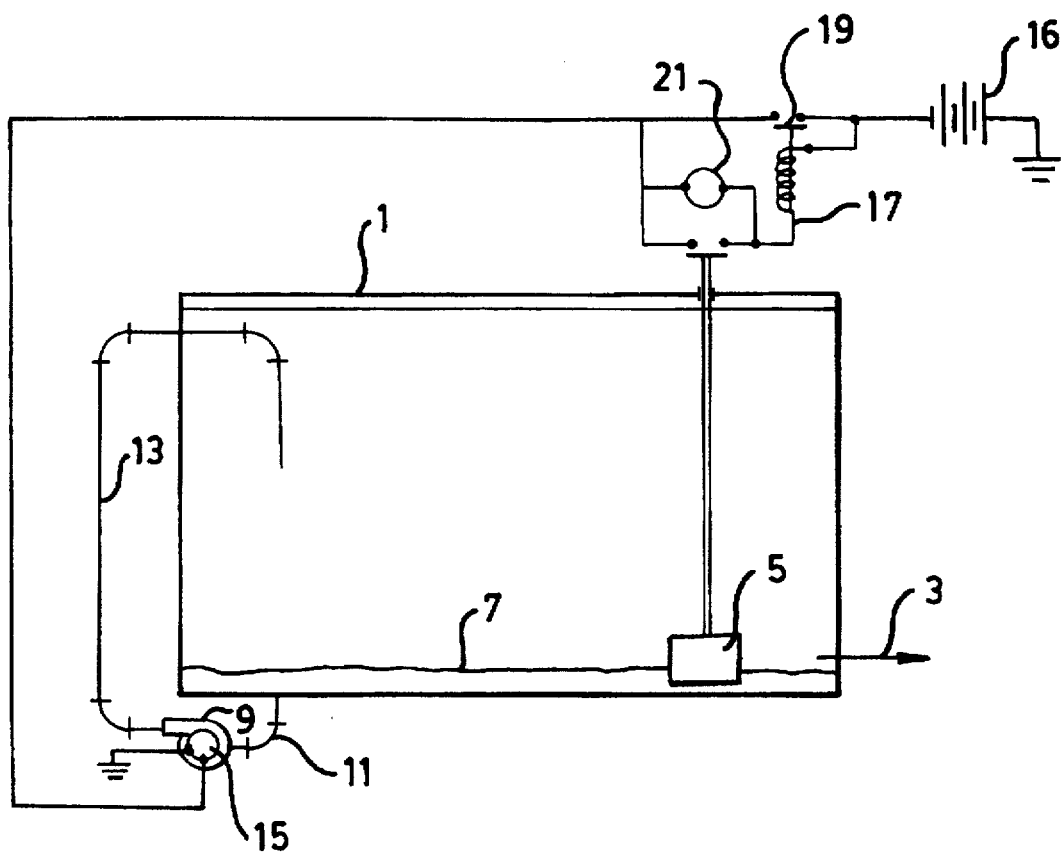

APPARATUS AND METHOD FOR DETECTING AND HANDLING LIQUID SEPARATION IN LIQUID EMULSIONS

TECHNICAL FIELD

The invention relates to an apparatus and method for detecting and handling separation of liquids in a liquid emulsion and more particularly to a device and method for preventing separated liquid disposed in the lower portion of a tank storing an emulsion form being withdrawn via a withdrawal conduit disposed in the lower portion of the tank. Emulsions of different density liquids stored in a tank tend to have the different density liquids coalesce, resulting in the heavy liquid concentrating at the bottom of the tank. If the emulsion is oil and water and it is used as a fuel when just water is withdrawn from the tank there will be no combustion so it is necessary to always withdraw the emulsion.

BACKGROUND ART

The separation of liquid emulsions of different density liquids such as oil and water are well known U.S. Pat. No. 3,344,659 describes an apparatus having a reservoir, a valved fluid inlet and a valved fluid outlet. A float within the reservoirs designed to be buoyantly supported at the interface between the two separated liquids such as oil and water. An indicator is carried by the float and cooperates with a recorder to provide a record of fluctuations in the height of the interface over a period of time. A control mechanism induces a sequence of valve operations where the inlet is opened and remains open until the incoming fluid has reached a particular level within the reservoir. The inlet is then closed and remains closed along with the outlet while separation of the liquids occurs. The outlet is then opened. The height of the interface provides an indication of the composition of the emulsion.

SUMMARY OF THE INVENTION

Among the objects of the invention may be noted the provision of an apparatus and method of detecting and handling the separation of high density liquid from an emulsion by preventing the high density liquid from being withdrawn from a withdrawal conduit disposed in fluid communication with the lower portion of the tank.

In general, an apparatus for preventing separated high density liquid from an emulsion of different density liquids stored in a tank from being withdrawn via a withdrawal conduit disposed in fluid communication with a lower portion of the tank, when made in accordance with this invention, is characterized by a float disposed within the tank. The float has a density which will cause it to sink in the emulsion and float on the high density liquid. A pump is disposed to take its suction from the lower portion of the tank and discharging adjacent the central portion of the tank and a drive is cooperatively associated with the float and pump to drive the pump when the float is lifted by an accumulation of the high density liquid in the lower portion of the tank, whereby the high density liquid is reemulsified and prevented from entering the withdrawal conduit.

A method of preventing separated higher density liquid form an emulsion of different density liquids stored in a tank from being withdrawn from a withdrawal conduit disposed adjacent the lower portion of the tank for drawing off the emulsified liquid from the tank, when performed in accordance with this invention is characterized by the steps of disposing within the tank, a float which floats on the higher density liquid and sinks in the emulsion, disposing a pump so that its suction is in fluid communication with the lowest portion of the tank and it discharges into the central elevation of the tank, and providing a drive cooperatively associated with the pump and the float so that when the float is lifted by an accumulation of higher density liquid in the lower portion of the tank, the drive operates the pump, whereby the high density liquid is reemulsified and prevented from entering the withdrawal conduit.

BRIEF DESCRIPTION OF THE DRAWINGS

The invention as set forth in the claims will become more apparent by reading the following detailed description in conjunction with the accompanying drawing in which:

The Sole FIGURE is a schematic view of an apparatus for preventing separated high density liquid from an emulsion of different density liquids stored in a tank from being withdrawn via a withdrawal conduit disposed in fluid communication with a lower portion of the tank.

DESCRIPTION OF THE PREFERRED EMBODIMENT

Referring now to the drawings in detail and in particular to the Sole FIGURE there is shown a schematic view of an apparatus and method for preventing separated higher density liquid form an emulsion of different density liquids stored in a tank 1 from being withdrawn from a withdrawal conduit 3 disposed adjacent the lower portion of the tank 1 for drawing off the emulsified liquid from the tank 1.

The apparatus comprises a float 5 disposed within the tank 1 and having a density which will causes it to sink in the emulsion and float on the high density liquid. The interface of the high density liquid and emulsion is indicated at 7. A pump 9 is disposed to take its suction from the lower portion of the tank 1 via a conduit or pipe 11 and discharges in the tank 1 via the conduit or pipe 13 which terminates adjacent the central portion of the tank 1. The discharge is disposed adjacent the central portion of the tank 1 to reemulsify high density fluid and prevent air entrapment in the emulsion.

An electric motor or drive 15 is coupled to the pump 9 to drive the pump 9. The electric motor 15 is preferably a DC motor and power is supplied by a battery 16, however an AC motor and power supply could be utilized. The capacity or output of the pump 9 is generally equivalent to ¹/₂₄ of the volume of the tank 1 per hour or sufficient to pump the volume of the tank in 24 hours. The discharge head of the pump 9 is sufficient to ensure that the separated high density liquid is reemulsified.

A relay or other type of switch 17 is cooperatively associated with the float 5 and electric motor 15 to drive the pump 9. When the float 15 is lifted a predetermined amount by the accumulation of high density liquid at the bottom of the tank 1 it activates the relay 17 closing a switch portion 19 within the relay 17 to run the pump and reemulsify the high density liquid as it is pumped back into the emulsion.

A time delay 21 is cooperatively associated with the relay 17 to hold the switch portion 19 closed a predetermined time as the accumulated high density liquid is being pumped from the bottom of the tank 1 and into the emulsion. The pump 9 is run for a predetermined period of time, insuring that all of the separated liquid has been removed from the bottom of tank 1 and reemulsified. The length of time that the pump 9 runs is dependent on the size of the tank the volume of accumulated high density liquid required to lift the float 5 and activate the relay 17 and the disposition of a withdrawal conduit 3 in the lower portion of the tank 1.

A method of preventing separated higher density liquid form an emulsion of different density liquids stored in the tank 1 from being withdrawn from a withdrawal conduit 3 disposed adjacent the lower portion of the tank 1 for drawing off the emulsified liquid from the tank is characterized by the steps of disposing within the tank 1, the float 5 which floats on the higher density liquid and sinks in the emulsion, disposing the pump 9 so that its suction is in fluid communication with the lower portion of the tank 1 and the pump 9 discharges into the central elevation of the tank 1, and providing the electric motor or other drive 15 cooperatively associated with the pump 9 and the float 5 so that when the float 5 is lifted by an accumulation of higher density liquid in the lower portion of the tank 1, the electric motor 15 operates the pump 9.

The relay or other type of switch 17 is provided and is cooperatively associated with the electric motor 15 and the float 5 so that when the float 5 is lifted by the higher density liquid a predetermined amount, the relay 17 starts the electric motor 15 and the pump 9.

The time delay 21 is cooperatively associated with the relay 17 to keep the electric motor 15 and pump 9 running a predetermined period of time after they were started, whereby the accumulated high density liquid is removed from the bottom of the tank 1 and reemulsified preventing separated high density fluid from entering the withdrawal conduit 3.

While the preferred embodiments described herein set forth the best mode to practice this invention presently contemplated by the inventor, numerous modifications and adaptations of this invention will be apparent to others skilled in the art. Therefore, the embodiments are to be considered as illustrative and exemplary and it is understood that the claims are intended to cover such modifications and adaptations as they are considered to be within the spirit and scope of this invention.

INDUSTRIAL APPLICABILITY

An apparatus and method for preventing separated higher density liquid form an emulsion of different density liquids stored in the tank 1 from being withdrawn from a withdrawal conduit 3 disposed adjacent the lower portion of the tank 1 for drawing off the emulsified liquid from the tank when made and performed in accordance with this invention advantageously is reliable and economical to manufacture, operate and maintain.

What is claimed is:

1. A method of preventing separated higher density liquid from an emulsion of different density liquids stored in a tank 1 from being withdrawn from a withdrawal conduit 3 disposed adjacent the lower portion of the tank 1 for drawing off the emulsified liquid from the tank characterized by the steps of disposing within the tank 1, a float 5 which floats on the higher density liquid and sinks in the emulsion, disposing a pump 9 so that its suction is in fluid communication with the lowest portion of the tank 1 and it discharges into the central portion of the tank 1, and providing a drive 15 cooperatively associated with the pump 9 and the float 5 so that when the float 5 is lifted by an accumulation of higher density liquid in the lower portion of the tank 1, the drive 15 operates the pump 9, whereby the high density liquid is removed from the bottom of the tank 1 and introduced into the central portion of the tank 1 where the high density fluid is reemulsified and prevented from entering the withdrawal conduit 3.

2. The method of claim 1, further characterized by providing an electric motor 15 for driving the pump 9.

3. The method of claim 2, further characterized by providing a switch 17 cooperatively associated with the electric motor 15 and the float 5 so that when the float 5 is lifted by the higher density liquid a predetermined amount, the switch 17 starts the electric motor 15 and the pump 9.

4. The method of claim 3, further characterized in that the switch 17 is a relay 17.

5. The method of claim 4, further characterized by providing a time delay 21 cooperatively associated with the relay 17 to run the electric motor 15 and pump 9 a predetermined period of time.

6. The method of claim 1, further characterized by providing the pump 9 with a capacity that is generally equivalent to 1/24 of the volume of the tank per hour.

* * * * *